US00PP23926P2

(12) United States Plant Patent
Danziger

(10) Patent No.: US PP23,926 P2
(45) Date of Patent: Sep. 24, 2013

(54) ***IMPATIENS* PLANT NAMED 'DHAR320'**

(50) Latin Name: *Impatiens hawkeri×flaccida*
Varietal Denomination: DHAR320

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 9 days.

(21) Appl. No.: 13/506,200

(22) Filed: Apr. 2, 2012

(51) Int. Cl.
*A01H 5/00* (2006.01)

(52) U.S. Cl.
USPC ..... Plt./317

(58) Field of Classification Search
USPC ..... Plt./317, 318.5, 318.6
See application file for complete search history.

*Primary Examiner* — Kent L Bell
(74) *Attorney, Agent, or Firm* — Cassandra Bright

(57) ABSTRACT

A new and distinct *Impatiens* cultivar named 'DHAR320' is disclosed, characterized by distinctive large magenta flowers, good branching and sun resistance. The new variety is an *Impatiens* normally produced as an outdoor ornamental plant for containers or gardens.

2 Drawing Sheets

Figure 1:
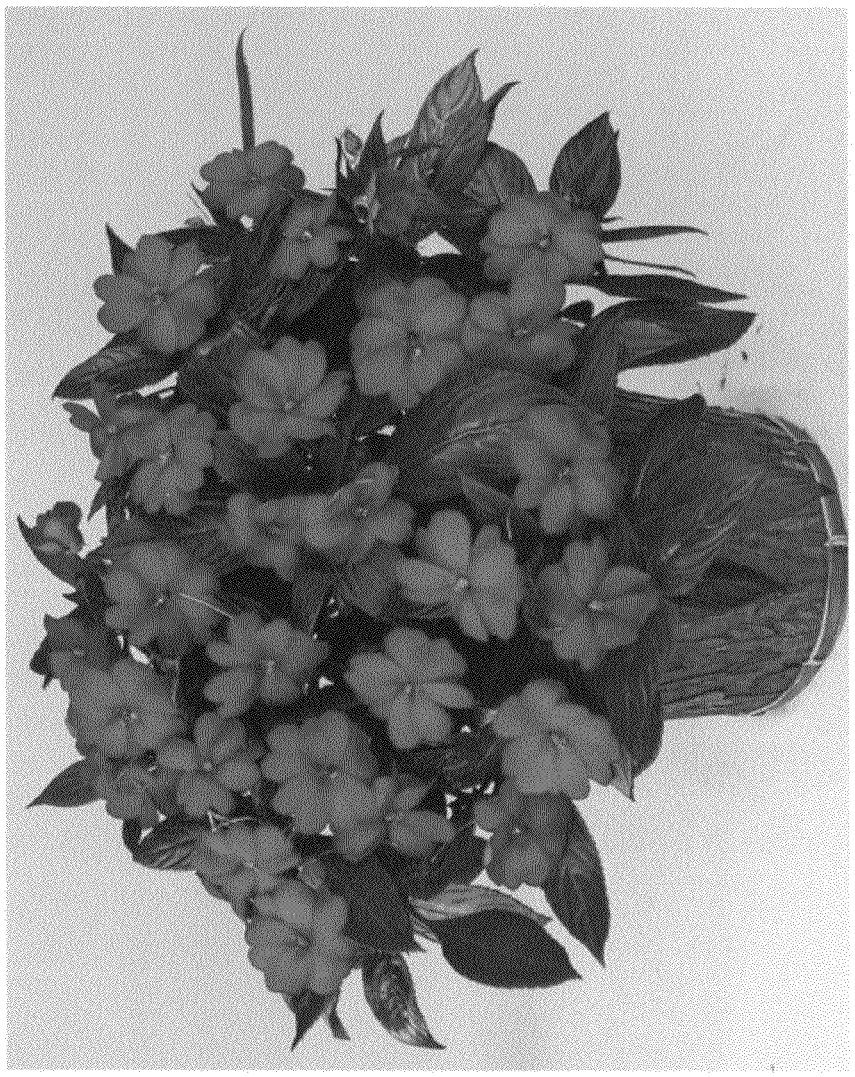

Latin name of the genus and species: *Impatiens hawkeri× flaccida.*

Variety denomination: 'DHAR320'.

BACKGROUND OF THE INVENTION

The new *Impatiens* cultivar is a product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during February of 2006.

The seed parent is the unpatented, proprietary variety referred to as *Impatiens* '460'. The pollen parent is the unpatented proprietary variety referred to as *Impatiens* '858'. The new variety was discovered in March of 2007 by the inventor in a group of seedlings resulting from the 2006 crossing, in a research greenhouse in Moshav Mishmar Hashiva, Israel.

Asexual reproduction of the new cultivar 'DHAR320' by leaf cuttings was first performed at a research greenhouse in Moshav Mishmar Hashiva, Israel in March of 2007 and has shown that the unique features of this cultivar are stable and reproduced true to type in successive generations.

SUMMARY OF THE INVENTION

The cultivar 'DHAR320' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHAR320' These characteristics in combination distinguish 'DHAR320' as a new and distinct *Impatiens* cultivar:

1. Large flowers.
2. Magenta flower color.
3. Good branching.
4. Sun resistance.

Plants of the new cultivar 'DHAR320' are similar to plants of the seed parent, *Impatiens* '460' in most horticultural characteristics, however, plants of the new cultivar 'DHAR320' have darker foliage, more vigorous growth habit, and larger flowers. Also plants of 'DHAR320' produce magenta colored flowers compared to the purple colored flowers of '460'.

Plants of the new cultivar 'DHAR320' are similar to plants of the pollen parent, *Impatiens* '858' in most horticultural characteristics, however, plants of the new cultivar 'DHAR320' produces magenta colored flowers compared to the purple flowers produced by '858'. Plants of 'DHAR320' also have a more vigorous growth habit and smaller flowers than '858'.

COMMERCIAL COMPARISON

Plants of the new cultivar 'DHAR320' are comparable to the variety *Impatiens* 'MisatoFG3', U.S. Plant Pat. No. 17,662. The two *Impatiens* varieties are similar in most horticultural characteristics however, the new variety 'DHAR320' differs in having darker colored flowers, and an overall more compact plant habit. Additionally, the new variety has larger flowers than 'MisatoFG3'.

Plants of the new cultivar 'DHAR320' can also be compared to the commercial variety *Impatiens* 'SAKIMP016', U.S. Plant Pat. No. 21,769. These varieties are similar in most horticultural characteristics, however 'DHAR320' has a more vigorous growth habit and larger flower size. Also plants of 'DHAR320' produce a lighter colored flower than flowers produced by plants of 'SAKIMP016'.

BRIEF DESCRIPTION OF THE PHOTOGRAPHS

The accompanying photograph in FIG. 1 illustrates in full color a typical plant of 'DHAR320' grown in a greenhouse, in a 16 cm pot. Age of the plant photographed is approximately 14 weeks from a leaf cutting.

Figure 2:
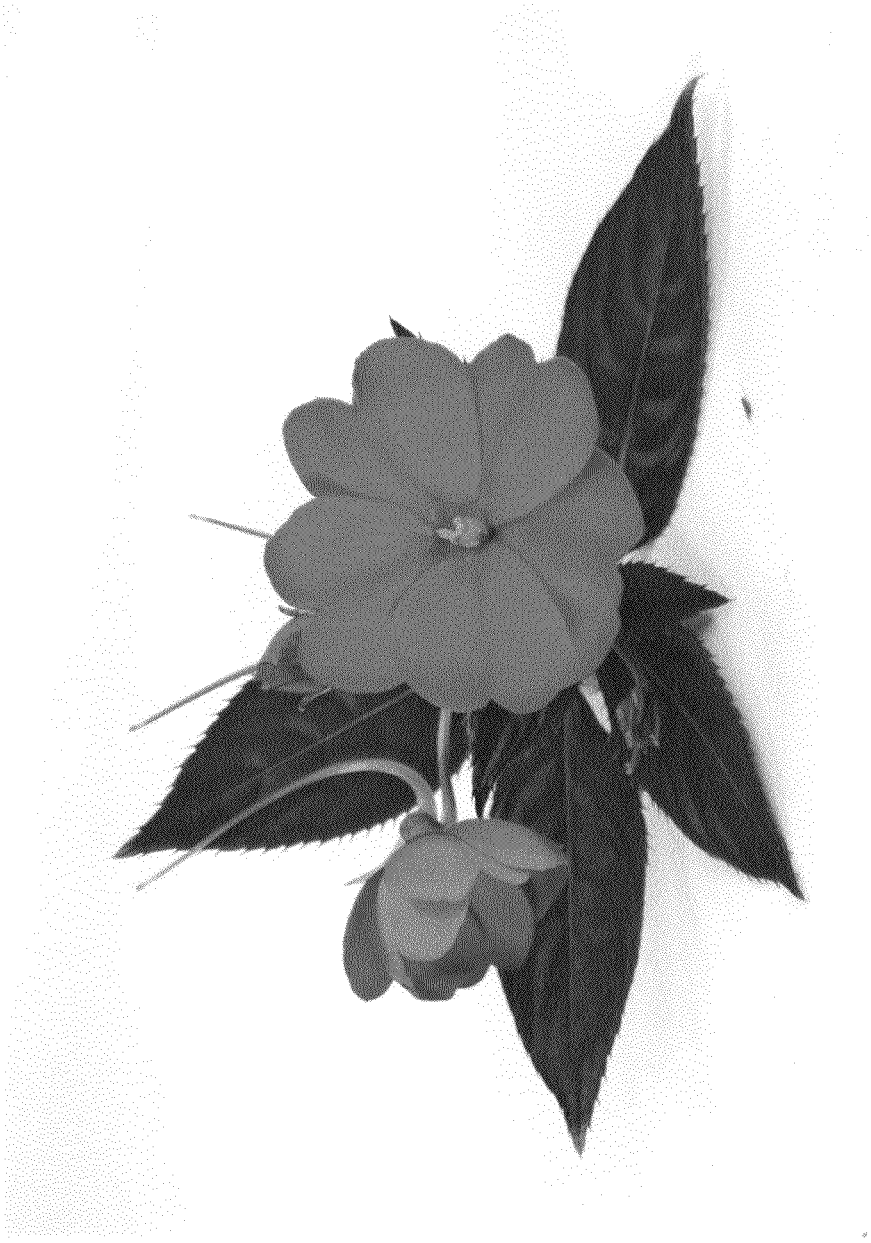

FIG. 2 illustrates in full color a close up of a typical bloom of 'DHAR320'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2005 except where general terms of ordinary dictionary significance are used. The following observations and measurements describe 'DHAR320' plants grown in a greenhouse during Winter and Spring in Moshav Mishmar Hashiva, Israel. The growing temperature ranged from 15° C. to 26° C. during the day and from 13° C. to 16° C. during the night. General light conditions are bright, normal sunlight. Measurements and numerical values represent averages of typical plant types.

Botanical classification: *Impatiens hawkerix flaccida 'DHAR*320'.

PROPAGATION

Time to initiate roots:
- *Summer.*—10 to 12 days at approximately 25° C.
- *Winter.*—14 to 20 days at approximately 18° C.

Root description: Fibrous adventitious roots.

PLANT

Growth habit: Mounded.
Pot size of plant described: 16 cm.
Age of plant described: Approximately 14 weeks from a rooted cutting.
Height: 30 cm.
Plant spread: 50 cm.
Growth rate: Vigorous.
Branching characteristics: Highly branched.
Length of primary lateral branches: 27 cm.
Quantity of primary lateral branches: 5-7.
Characteristics of primary lateral branches:
- *Form.*—Oval shape.
- *Diameter.*—1 cm.
- *Color.*—Green group 137 RHS.
- *Texture.*—Smooth.
- *Strength.*—Strong.

Internode length: 7 cm.

FOLIAGE

Leaf:
- *Arrangement.*—Alternate.
- *Quantity.*—Approximately 20-25 per branch.
- *Average length.*—8 cm.
- *Average width.*—3.5 cm.
- *Shape of blade.*—Lanceolate to ovate.
- *Apex.*—Attenuate.
- *Base.*—Acuminate.
- *Margin.*—Ciliate.
- *Texture of top surface.*—Smooth.
- *Pubescence.*—None.
- *Aspect.*—45 degrees.
- *Color.*—Young foliage upper side: Green Group 137 B RHS. Young foliage under side: Greyed Green Group 194 B RHS. Mature foliage upper side: Yellow Green Group 147 A RHS. Mature foliage under side: Yellow Green Group 147 C RHS.
- *Venation.*—Midrib with secondary veins. Pinnate, only lower surface. Type: Pinnate. Venation color upper side: Yellow Green Group 147 C RHS. Venation color under side: Red Purple Group 60 A RHS.
- *Petiole.*—Length: 0.6 cm. Diameter: 0.3 cm. Color: Greyed Red Group 181C RHS. Texture: Smooth.

FLOWER

Natural flowering season: Flowers at any day length. All year round in a greenhouse environment. Flowering is continuous from spring until fall in an outdoor garden.
Days to flowering from rooted cutting: 10 weeks.
Inflorescence and flower type and habit: Single flowers raised above the foliage. The corolla consists of five petals.
Rate of flower opening: 10 to 15 days from bud to fully opened flower.
Flower longevity on plant: 5-8 Days.
Persistent or self-cleaning: Self cleaning.

Bud:
- *Shape.*—Ovate.
- *Length.*—1.5 cm.
- *Diameter.*—0.8 cm.
- *Color.*—Red Purple Group 61 C RHS.

Flower size:
- *Diameter.*—8 cm.
- *Depth.*—About 6.0 cm, including spur.

Petals:
- *Quantity.*—5.
- *Arrangement.*—Rotate, overlapping.
- *Length.*—4 cm.
- *Width.*—3.5 cm.
- *Shape.*—Obcordate.
- *Apex.*—Heart Shape.
- *Base.*—Acute.
- *Margin.*—Entire.
- *Texture, upper and lower surfaces.*—Smooth.
- *Color.*—Magenta. When opening, upper surface: Red Purple Group N66A RHS. When opening, lower surface: Red Purple Group N66B RHS. Fully opened, upper surface: Red Purple Group N66A RHS. Fully opened, lower surface: Red Purple Group N66B RHS.

Spurs:
- *Quantity per flower.*—1.
- *Length.*—6 cm.
- *Diameter.*—0.1 cm.
- *Aspect.*—Spur curvature 40°-45° from peduncle.
- *Color.*—Towards base: Red Purple Group 63A RHS. Apex: Yellow Green Group 145A RHS.

Sepals:
- *Quantity.*—2.
- *Length.*—1.5 cm.
- *Width.*—0.5 cm.
- *Shape (overall).*—Oblong. Apex: Acute. Base: Rounded.
- *Margin.*—Entire.
- *Color.*—Red Group 54 C RHS.

Peduncles:
- *Length.*—6.5 cm.
- *Diameter.*—0.2 cm.
- *Angle.*—About 45° to the lateral branch.
- *Strength.*—Stable, flexible.
- *Texture.*—Smooth.
- *Color.*—Yellow Green Group 144 D RHS.

Fragrance: None.

REPRODUCTIVE ORGANS

Stamens: There are five stamens with introrse anthers that are more or less fused and form a cap over the ovary.

*Number.*—5.

Anthers:

*Shape*.—Oblong.

*Length*.—Approximately 0.4 cm.

*Color*.—Red Purple Group 61 B RHS.

*Pollen*.—Color: White Group 155 D RHS. Quantity: Many.

Pistil:

*Number.*—1.

*Length.*—0.5 cm.

*Style*.—Length: 0.5 cm. Color: Yellow Green Group 144 A RHS.

*Stigma*.—Shape: Round. Color: White Group N 155B RHS. Ovary Color: Yellow-Green group, 144D RHS.

OTHER CHARACTERISTICS

Seeds and fruits: Minute locule fruits produce 5-10 seeds per fruit.

Disease/pest resistance: Neither resistance nor susceptibility has been observed.

Temperature tolerance: Grows best at a range between 10° C.-30° C. Will tolerate moderate temperatures outside of this range.

What is claimed is:

1. A new and distinct cultivar of *Impatiens* plant named 'DHAR320' as herein illustrated and described.

* * * * *